United States Patent
Launay et al.

(10) Patent No.: US 7,170,533 B2
(45) Date of Patent: Jan. 30, 2007

(54) METHOD AND DEVICE FOR IMAGING WITH REORIENTATION OF AN OBJECT

(75) Inventors: Laurent Launay, Saint Remy les Chevreuse (FR); Yves Lucien Marie Trousset, Palaiseau (FR); Cyril Riddell, Paris (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 36 days.

(21) Appl. No.: 10/757,859

(22) Filed: Jan. 15, 2004

(65) Prior Publication Data
US 2005/0022158 A1   Jan. 27, 2005

(30) Foreign Application Priority Data
Jan. 30, 2003   (FR) .................................. 03 01046

(51) Int. Cl.
*G09G 5/00*   (2006.01)
(52) U.S. Cl. ........................ 345/649; 345/650
(58) Field of Classification Search ................ 382/132; 345/649–653
See application file for complete search history.

(56) References Cited

U.S. PATENT DOCUMENTS 5,019,809 A * 5/1991 Chen ...................... 340/815.42
5,588,097 A * 12/1996 Ono et al. .................. 345/653
5,704,791 A * 1/1998 Gillio ......................... 434/262
5,956,045 A * 9/1999 Gotoh et al. ................ 345/655
6,342,889 B1   1/2002 Callahan

FOREIGN PATENT DOCUMENTS

EP   0 397 904 A1   11/1990
EP   0 397 851 A    5/2000

OTHER PUBLICATIONS

Van Der Weide, R. et al., "CTA-Based Angle Selection for Diagnostic and Interventional Angiography of Saccular Intracranial Aneurysms", IEEE Trans. on Mecial Imaging, vol. 17, No. 5, Oct. 1998, pp. 831-841.

* cited by examiner

*Primary Examiner*—Kee M. Tung
*Assistant Examiner*—Michelle K. Lay
(74) *Attorney, Agent, or Firm*—Cantor Colburn LLP

(57) ABSTRACT

A medical imaging device and method having a display screen, a processor for processing image data in order to display the data in the form of a 3D model, and a user interface. The processor acquires at least two points positioned in the 3D model via the user interface; deduces the positioning of an axis defined by the two points in the 3D model, and reorients the 3D model in such a manner that the axis as indicated in this way is to be found in a predefined orientation relative to the plane of the display screen.

49 Claims, 3 Drawing Sheets

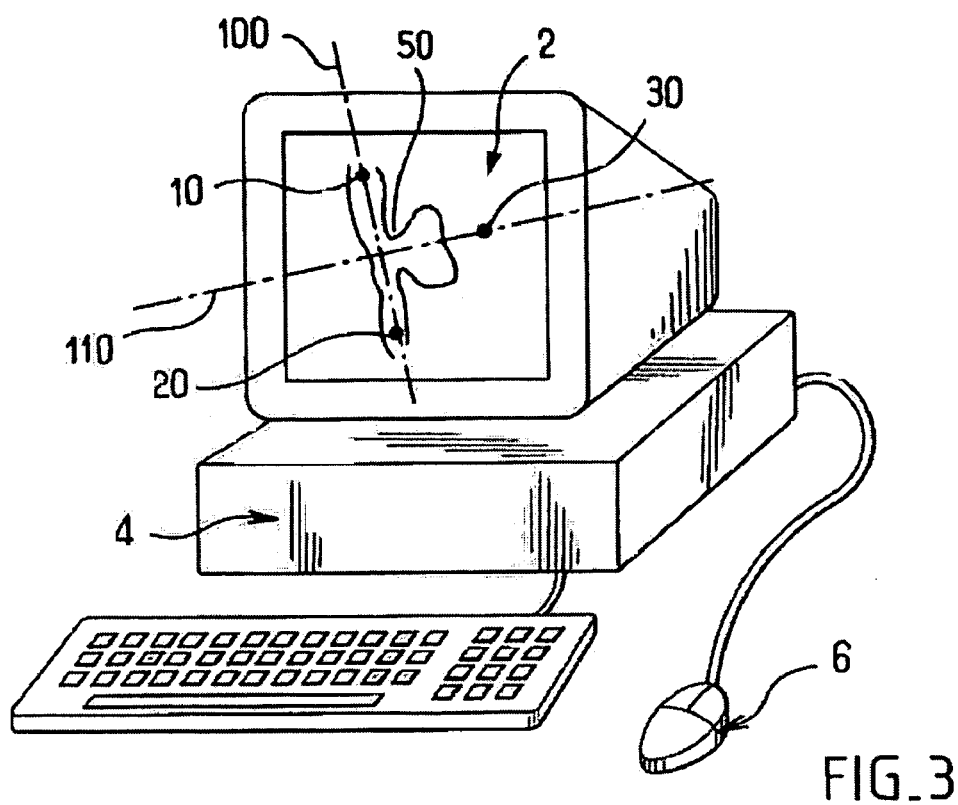
FIG_3
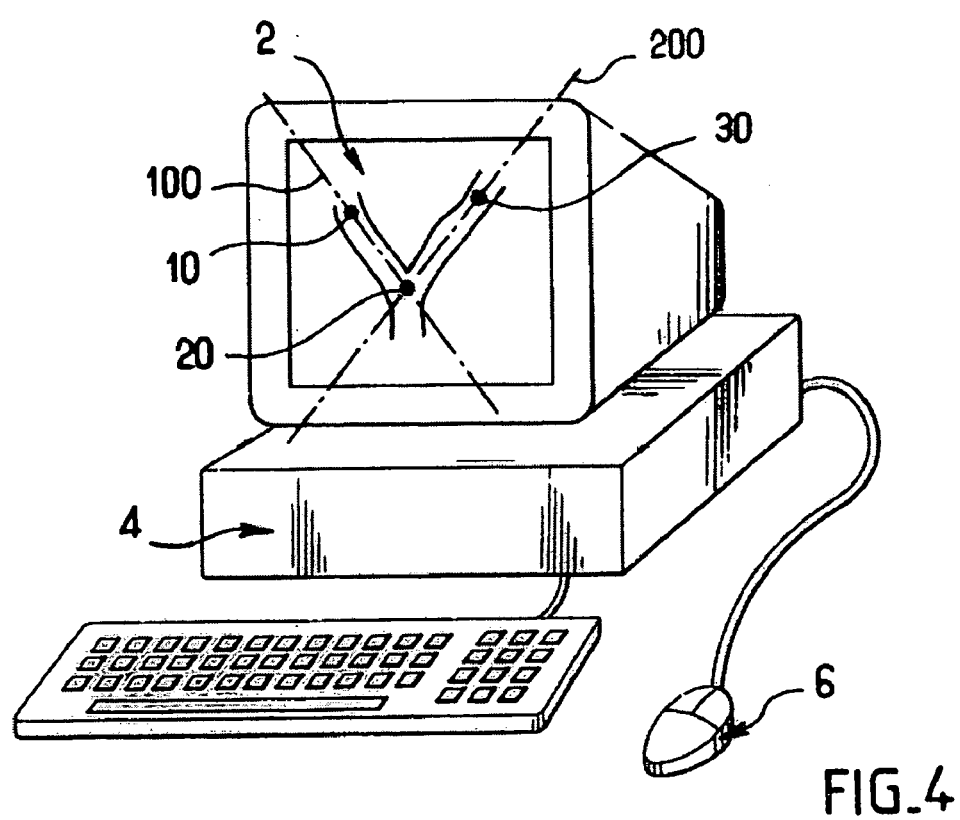
FIG_4

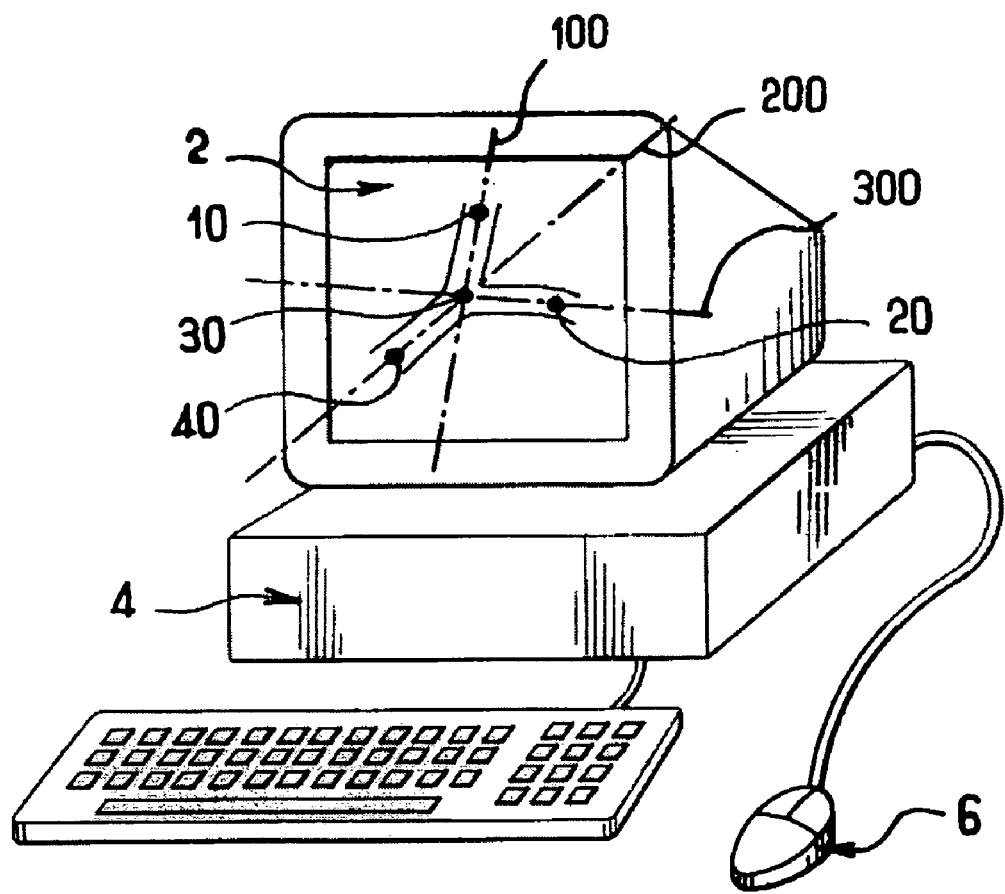
FIG_5

METHOD AND DEVICE FOR IMAGING WITH REORIENTATION OF AN OBJECT

CROSS-REFERENCE TO RELATED APPLICATIONS

This application claims the benefit of a priority under 35 USC 119(a)–(d) to French Patent Application No. 03 01046 filed Jan. 30, 2003, the entire contents of which are hereby incorporated by reference.

BACKGROUND OF THE INVENTION

An embodiment of the invention relates to displaying three-dimensional (3D) images of an object that may be acquired in radiology, and in particular to representing anatomical sites in preparation for, or even during, a therapeutic act performed by interventional radiology or by surgery.

More particularly, an embodiment of the invention relates to tools enabling an optimum orientation to be identified for a biological object represented in three dimensions or enabling an optimum selection to be made for presenting a section of such an object on a display, such as a screen.

In the field of interventional radiology, therapeutic tools are presently deployed and moved under fluoroscopic guidance. To do this, it is desired visually to find an appropriate working view by orienting the imaging system, where such orientation provides a suitable display of the pathology to be treated. With complex pathologies such as cerebral aneurysms, it is difficult for a radiologist or other practitioner to find such a suitable working view.

Prior to the introduction of three-dimensional tools in angiography theaters, it was typically the practice to take a series of recordings or acquisitions under different angles selected empirically until a satisfactory view was obtained. That approach had several drawbacks, and in particular the high dose of radiation, such as X-rays, administered to the patient and also the high dose of injected contrast media. Furthermore, the time devoted to that procedure could be lengthy.

With the introduction of tools with three-dimensional representation, the preferred technique for selecting the working view has been transformed considerably. In a first step, 3D acquisition is performed, and then the radiologist examines the image displayed on a computer screen in three dimensions while interactively applying rotations to the 3D model until an acceptable view is found. In a second step, the user transmits the selected angle of observation to a radiological acquisition system as a control parameter for automatically moving the gantry until the desired working view is obtained.

Interactive rotation of the image in three dimensions has the advantage of not requiring repeated doses of X-rays and of not requiring repeated doses of contrast medium. Nevertheless, the quality of the result depends essentially on the skill of the user in interactively rotating the three-dimensional image. In addition, that technique does not save a significant amount of time compared with the earlier techniques. Furthermore, that technique does not ensure that the selected working view is the optimum view, given that the selection is based essentially on the skill of the user in manipulating a 3D image. In other words, there might be some other direction of observation that is better than that found by the user, but which the user did not find.

BRIEF DESCRIPTION OF THE INVENTION

An embodiment of the invention provides a three-dimensional radiological display system enabling a working view to be positioned easily, regardless of whether the view is three-dimensional or in section.

In an embodiment of the invention, an imaging device comprises: means for display; means for processing image data in order to display the data in the form of a 3D model, and a user interface; the means for processing acquires at least two points positioned in the 3D model via the user interface, to deduce the positioning of an axis defined by the two points in the 3D model, and to reorient the 3D model such that the axis is in a predefined orientation relative to a plane of the means for display.

An embodiment of the invention also provides a method of displaying a 3D model imaging, the method comprising: providing means for display; providing means for processing image data in order to display the data in the form of a 3D model; providing a user interface fitted to the means for processing; positioning at least two points in the 3D model by means of the user interface; causing the means for processing to deduce therefrom a position of an axis defined by the points on the 3D model; and causing the means for processing to reorient the 3D model such that the axis lies in a predefined orientation relative to a plane of the means for display.

An embodiment of the invention provides a computer program carrier comprising code means that when executed on a computer carry out the aforementioned method of the means for processing. Alternatively, an embodiment of the invention provides a computer program carrier carrying code that when executed on a computer carry out the aforementioned method of the means for processing.

BRIEF DESCRIPTION OF THE DRAWINGS

The invention and embodiments thereof will be better understood when read with the following detailed description made with reference to the accompanying figures, in which:

FIG. 3 shows a system for displaying an aneurysm using three points that define two axes;

FIG. 4 shows a system for displaying a V-shaped bifurcation using three points defining two axes; and FIG. 5 shows a system for displaying a Y-shaped bifurcation using four points defining three axes.

DETAILED DESCRIPTION OF THE INVENTION

Figure 1:
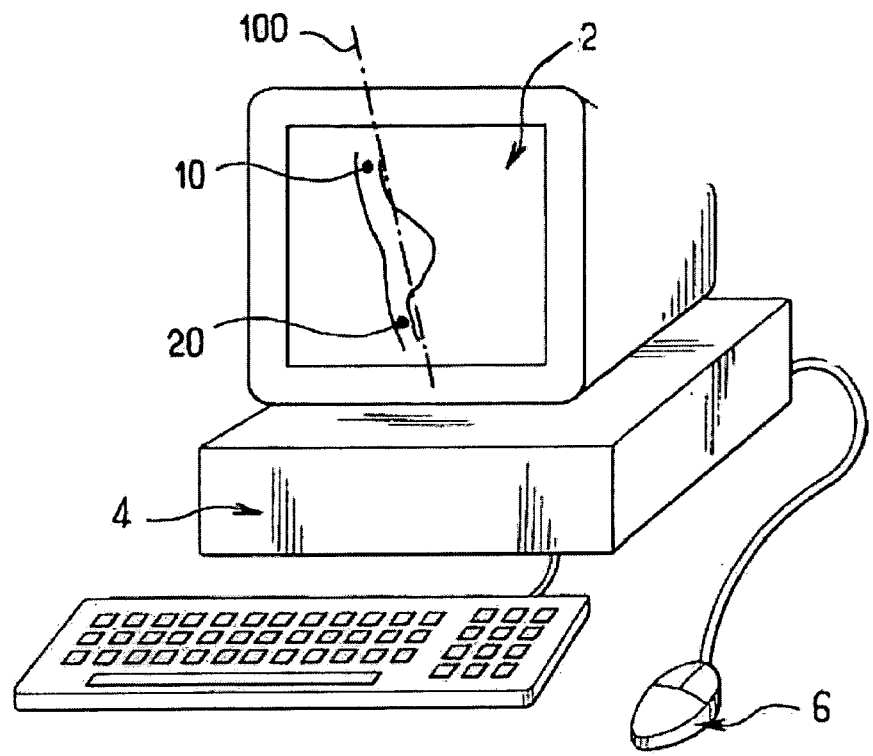
FIG. 1 shows a system once a user has placed two points on a 3D model.

An embodiment is described with reference to FIGS. 1 and 2. In this embodiment, a user seeks to find the best working view on a three-dimensional model of a cerebral aneurysm, which model is obtained by previously performing image acquisition on the patient; this acquisition can be implemented, for example, by means of magnetic resonance imagery (MRI), a scanner, or an angiography theater.

In this embodiment, the system comprises means for display, such as screen 2; means for processing, such as image-processing processor 4; and means for providing a control interface, i.e., interactive manual interface, in this case a computer mouse 6.

In this embodiment, the system proposes a display of an anatomical zone in the form of a 3D model. For example, the anatomical zone may be a blood vessel carrying an aneurysm in some arbitrary orientation. The aneurysm appears to be a slight bulge on the margin of the vessel carrying it. The user is then invited to position an axis 100 modeling the main positioning of the carrying vessel. To do this, the user places two points on the carrying vessel at two distinct locations, preferably on opposite sides of the aneurysm. These two points 10 and 20 are placed, for example, by using two cross-section views of the carrying vessel, the views being located on either side of the aneurysm.

The two points in this embodiment or the points in further embodiments can also be positioned in some other way, for example on 3D images obtained using surface rendering techniques, volume rendering techniques, or maximum intensity projection (MIP).

From the two points, the means for processing 4, i.e., the image processing processor, identifies an axis 100 within the three-dimensional model in its initial display on the screen. After this axis 100 has been positioned, the processor reprocesses the displayed image so that the three-dimensional model is subjected to a rotation, which rotation causes the axis as previously defined manually to be brought into alignment parallel with the plane of the display screen. This first rotation can be automatic and is typically the shortest rotation that serves to bring the axis into alignment with the screen, being close to a direct projection of the axis onto the screen.

The processor is then configured to implement image processing under manual control of the user, using the previously-defined axis as a reference. In the present example, the user moves the mouse 6 progressively so as to cause the three-dimensional model to move progressively about the previously defined axis 100.

The carrying vessel and its aneurysm are thus seen to pivot progressively about the axis of the carrying vessel while the user continues to examine it visually.

The user can thus easily identify the ideal position in pivoting, and after making several turns in opposite directions about the optimum position, the user freezes the mouse in the optimum position. The user then has the best view of the aneurysm.

Figure 2:
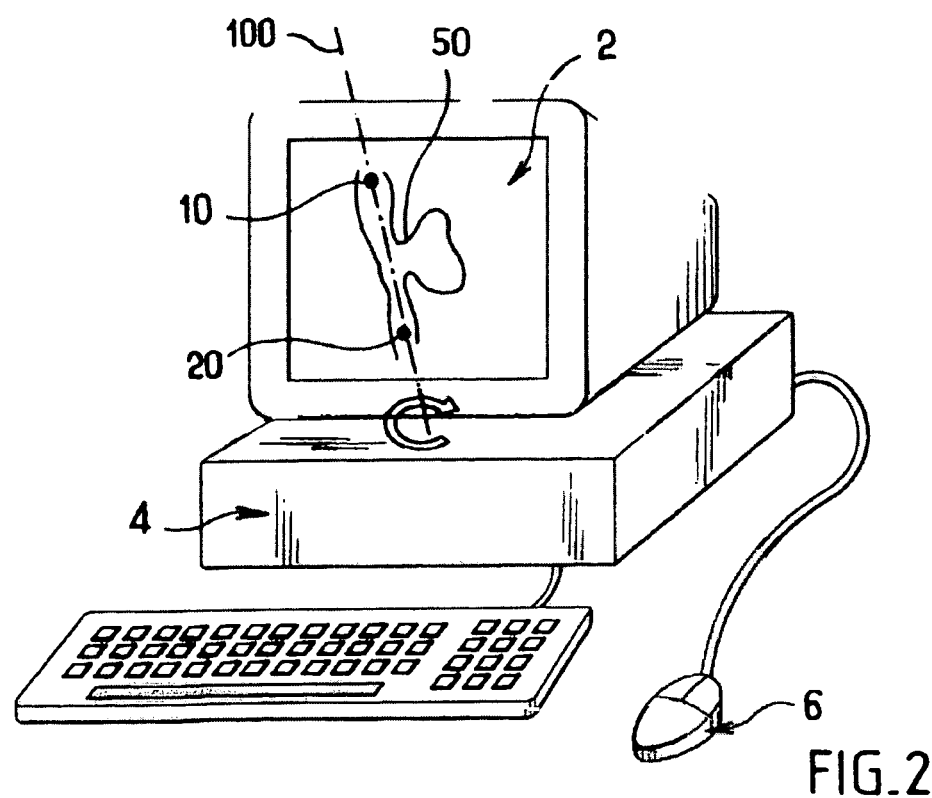
FIG. 2 shows a system after reorientation on the basis of the points positioned by the user.

This best view is, for example, the view that enables the portion 50 of the aneurysm (referred to as its "collar") to be seen most clearly, which portion is shown in FIG. 2.

The resulting image can then be considered as being optimal by the user and can be taken into account by the system as the working view to be adopted.

The processor identifies the current parameters defining the orientation of the three-dimensional model as the display parameters to be adopted either merely for subsequent display or else during a forthcoming medical intervention.

In this and other embodiments, the identification of the optimum orientation is followed by a command for repositioning a radiation detector relative to the body of the patient. Thus, the optimum orientation selected on the screen subsequently defines the image rotation to be retranscribed by the processor in the form of a physical orientation to be given to the detector. Once this physical reorientation has been adopted by the detector (the sensor then lying parallel with the carrying vessel), the detector supplies an image that corresponds precisely to the orientation selected by the user, this image being without reprocessing.

An embodiment of the invention makes it possible not only to position a 3D model on a computer screen, but also to orient the arch in a vascular theater with the corresponding angle. It thus comprises a device which serves not only to reorient a model on a screen, but which is capable also, at the request of the user, of controlling the mechanical movement of an image acquisition system so that the system takes up the determined angle.

Intervention can then be performed on the aneurysm with the anatomical region of the intervention being displayed continuously with the best viewing angle. In this embodiment, the system also makes it possible to select an optimum section view of the pathology under observation.

Thus, once the reference axis has been positioned by the user and the 3D model has been reoriented so that the axis is parallel to the screen, the image processor proposes a section position to the user under progressive displacement of the mouse 6. With the mouse, the user then moves a section plane parallel to the surface of the screen in depth, i.e., in depth in the object displayed.

Several other embodiments are possible, for example, by moving the section plane in translation parallel to the reference axis, or perpendicularly to the reference axis while still keeping it perpendicular to the screen.

The embodiment, as described above, is typically applied to displaying an aneurysm. Nevertheless, and in particular because this embodiment implements rotation about an axis defining a vessel, another application is observing a stenosis (a narrowing of a vessel). In that case also, by turning about a selected axis, it possible to find the view that reveals the depth of the narrowing as well as possible. The manually-placed axis, in the case of a vessel, could also be positioned on a needle that appears on the screen since it has been placed in the surgical zone under observation.

In addition to the above-described embodiment in which the user specifies only one reference axis manually, it is also possible for a plurality of axes to be defined manually. An example comprises positioning three points on the three-dimensional model so as to define between them two axes, the two axes defining a plane of observation. This plane is taken into account by the image processing processor in order to begin by reorienting the 3D model in such a manner that the plane lies parallel to the screen. The two axes as defined in this way are then both parallel to the screen.

It is also appropriate to use two reference axes for an aneurysm, thus enabling it to be reoriented (FIG. 3) on the basis not only of the two points 10 and 20 representing the carrying vessel, but also on the basis of an additional point 30 positioned on the aneurysm itself. In this particular case, the two axes enabling the 3D model to be repositioned automatically are thus the axis of the carrying vessel 100 and, for example, an axis 110 perpendicular to the axis of the vessel and passing through the additional point 30 situated on the aneurysm.

Another embodiment comprises reorienting a V-shaped bifurcation of two vessels (FIG. 4). Two axes 100 and 200 are then positioned using three points 10, 20, and 30 in order to represent each of the two bifurcations, the three-dimensional model being reoriented in such a manner that the two axes 100 and 200 are simultaneously parallel to the screen. A view of this bifurcation is then obtained in which the V-shape is at maximum spread. In this case also, the system is designed to propose displacement of successive sections in depth and parallel to the screen under manual control of the user. The two 3D axes 100 and 200 are kept parallel to the screen while displacing sections in this way.

In another embodiment as shown in FIG. 5, which is particularly adapted to displaying a Y-shaped bifurcation of vessels, the user defines three distinct axes 100, 200, and 300 by manually positioning four points 10, 20, 30, and 40. By placing three 3D axes on respective ones of the three branches of the Y-shaped bifurcation, the user provides the image processing processor with geometrical references representative of the positioning of each of the branches. The processor then optimizes the positioning of the display that is such that each of the three axes is as close as possible to being parallel with the surface of the screen.

The positioning of three axes can also be defined by some greater number of points, for example six points organized in three pairs, each defining one axis. In this case also, the user can displace a section plane progressively in depth parallel to the initial display, with the orientation of each of the three axes relative to the plane of the screen remaining constant.

The three-axis embodiment is also suitable for observing an aneurysm. The aneurysm may be considered as being ellipsoidal, and can be represented by its two main axes (longitudinal axis and transverse axis). The two axes are thus modeled manually by manually positioning two pairs of points. The third axis comprises, for example, the axis of the carrying vessel. The processor then reorients the 3D model so as to bring the three axes as close as possible to being parallel with the screen.

In this embodiment as in the preceding embodiments, provision is preferably made for the optimum view as established in this way to be transmitted in the form of a command for positioning the image sensor physically relative to the patient using motor-driven means.

One skilled in the art may propose or make various modifications to the structure/way and/or function and/or result and/or steps of the disclosed embodiments and equivalents thereof without departing from the scope and extant of the invention.

What is claimed is:

1. An imaging device comprising:
   means for display;
   means for processing image data in order to display the data in the form of a 3D model; and
   a user interface;
   wherein the means for processing is configured to acquire at least two points positioned in the 3D model via the user interface, to deduce the positioning of an axis defined by the two points in the 3D model, and to reorient the 3D model such that the axis is in a predefined orientation relative to a plane of the means for display; and
   wherein the means for processing is configured to orient the 3D model in such a manner that the axis defined by the two points indicated by the user is parallel to the plane of the means for display.

2. The device according to claim 1 comprising:
   means for positioning an image acquisition system relative to an object, which means implement positioning of the acquisition system to correspond with an orientation of the model as displayed on the means for display.

3. The device according to claim 2, the device being in command communication with an image sensor, the device further comprising:
   means for identifying a final orientation of the 3D model as confirmed by the user; and
   means for producing a command signal for physically orienting the image sensor relative to the user in correspondence with the final confirmed orientation.

4. The device according to claim 2 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

5. The device according to claim 2 wherein the means for processing implements rotation of the 3D model about the axis defined by the two points indicated by the user.

6. The device according to claim 2 wherein the means for processing acquires at least three points positioned in the 3D model by means of the user interface, to deduce two axes therefrom each passing through a pair of the points, and to reorient the 3D model in such a manner that the two axes are substantially parallel to the means for display.

7. The device according to claim 2 wherein the means for processing causes display of a section view of the 3D model on a section plane which presents a predefined orientation relative to the axis indicated by the user.

8. The device according to claim 7 wherein the means for processing moves the section plane progressively under control from the user interface.

9. The device according to claim 8 wherein the means for processing moves the section plane in the 3D model while keeping the section plane in a predefined orientation.

10. The device according to claim 7 wherein the means for processing moves the section plane in the 3D model while keeping the section plane in a predefined orientation.

11. The device according to claim 2 comprising:
    an image acquisition system; and
    means for orienting by controlling an angular position of the system to correspond with an orientation of the 3D model as defined on means for display.

12. The device according to claim 11 wherein the means for processing implements rotation of the 3D model about the axis defined by the two points indicated by the user.

13. The device according to claim 11 wherein the means for processing acquires at least three points positioned in the 3D model by means of the user interface, to deduce two axes therefrom each passing through a pair of the points, and to reorient the 3D model in such a manner that the two axes are substantially parallel to the means for display.

14. The device according to claim 11 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

15. The device according to claim 11, the device being in command communication with an image sensor, the device further comprising:
    means for identifying a final orientation of the 3D model as confirmed by the user; and
    means for producing a command signal for physically orienting the image sensor relative to the user in correspondence with the final confirmed orientation.

16. The device according to claim 11 wherein the means for processing causes display of a section view of the 3D model on a section plane which presents a predefined orientation relative to the axis indicated by the user.

17. The device according to claim 16 wherein the means for processing moves the section plane progressively under control from the user interface.

18. The device according to claim 1 wherein the means for processing implements rotation of the 3D model about the axis defined by the two points indicated by the user.

19. The device according to claim 18, the device being in command conununication with an image sensor, the device further comprising:
  means for identifying a final orientation of the 3D model as confirmed by the user; and
  means for producing a command signal for physically orienting the image sensor relative to the user in correspondence with the final confinned orientation.

20. The device according to claim 18 wherein the means for processing acquires at least three points positioned in the 3D model by means of the user interface, to deduce two axes therefrom each passing through a pair of the points, and to reorient the 3D model in such a manner that the two axes are substantially parallel to the means for display.

21. The device according to claim 18 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

22. The device according to claim 18 wherein the means for processing causes display of a section view of the 3D model on a section plane which presents a predefined orientation relative to the axis indicated by the user.

23. The device according to claim 22 wherein the means for processing moves the section plane progressively under control from the user interface.

24. The device according to claim 1 wherein the means for processing causes display of a section view of the 3D model on a section plane which presents a predefined orientation relative to the axis indicated by the user.

25. The device according to claim 24 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

26. The device according to claim 24 wherein the means for processing acquires at least three points positioned in the 3D model by means of the user interface, to deduce two axes therefrom each passing through a pair of the points, and to reorient the 3D model in such a manner that the two axes are substantially parallel to the means for display.

27. The device according to claim 24, the device being in command communication with an image sensor, the device further comprising:
  means for identifying a final orientation of the 3D model as confirmed by the user; and
  means for producing a command signal for physically orienting the image sensor relative to the user in correspondence with the final confirmed orientation.

28. The device according to claim 24 wherein the means for processing moves the section plane in the 3D model while keeping the section plane in a predefined orientation.

29. The device according to claim 28 wherein the means for processing acquires at least three points positioned in the 3D model by means of the user interface, to deduce two axes therefrom each passing through a pair of the points, and to reorient the 3D model in such a manner that the two axes are substantially parallel to the means for display.

30. The device according to claim 28, the device being in command communication with an image sensor, the device further comprising:
  means for identifying a final orientation of the 3D model as confirmed by the user; and
  means for producing a command signal for physically orienting the image sensor relative to the user in correspondence with the final confirmed orientation.

31. The device according to claim 28 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

32. The device according to claim 24 wherein the predefined orientation of the section plane is orientated parallel to the axis indicated by the user.

33. The device according to claim 32 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

34. The device according to claim 32 wherein the means for processing acquires at least three points positioned in the 3D model by means of the user interface, to deduce two axes therefrom each passing through a pair of the points, and to reorient the 3D model in such a manner that the two axes are substantially parallel to the means for display.

35. The device according to claim 32, the device being in command communication with an image sensor, the device further comprising:
  means for identifying a final orientation of the 3D model as confirmed by the user; and
  means for producing a command signal for physically orienting the image sensor relative to the user in correspondence with the final confirmed orientation.

36. The device according to claim 24 wherein the means for processing moves the section plane progressively under control from the user interface.

37. The device according to claim 36 wherein the means for processing moves the section plane in the 3D model while keeping the section plane in a predefined orientation.

38. The device according to claim 36 wherein the means for processing acquires at least three points positioned in the 3D model by means of the user interface, to deduce two axes therefrom each passing through a pair of the points, and to reorient the 3D model in such a manner that the two axes are substantially parallel to the means for display.

39. The device according to claim 36, the device being in command communication with an image sensor, the device further comprising:
  means for identifying a final orientation of the 3D model as confirmed by the user; and
  means for producing a command signal for physically orienting the image sensor relative to the user in correspondence with the final confirmed orientation.

40. The device according to claim 36 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

41. The device according to claim 1 wherein the means for processing acquires at least three points positioned in the 3D model by means of the user interface, to deduce two axes therefrom each passing through a pair of the points, and to reorient the 3D model in such a manner that the two axes are substantially parallel to the means for display.

42. The device according to claim 41 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

43. The device according to claim 41, the device being in command communication with an image sensor, the device further comprising:
   means for identifying a final orientation of the 3D model as confirmed by the user; and
   means for producing a command signal for physically orienting the image sensor relative to the user in correspondence with the final confirmed orientation.

44. The device according to claim 1 wherein the means for processing acquires a plurality of points, to deduce a plurality of axes therefrom that are not all mutually parallel, each passing through a different pair of points selected from the plurality of points, and to reorient the 3D model bringing the set of the axes as close as possible to parallel with the plane of the means for display.

45. The device according to claim 44, the device being in command communication with an image sensor, the device further comprising:
   means for identifying a final orientation of the 3D model as confirmed by the user; and
   means for producing a command signal for physically orienting the image sensor relative to the user in correspondence with the final confirmed orientation.

46. The device according to claim 1, the device being in command communication with an image sensor, the device further comprising:
   means for identifying a final orientation of the 3D model as continued by the user; and
   means for producing a command signal for physically orienting the image sensor relative to the user in correspondence with the final confirmed orientation.

47. A method for displaying a 3D model in imaging comprising:
   providing means for display;
   providing means for processing in order to display data in the form of a 3D model; and
   providing a user interface fitted to the means for processing;
   positioning at least two points in the 3D model by means of the user interface;
   causing the means for processing to deduce therefrom the position of an axis defined by the points on the 3D model; and
   causing the means for processing to reorient the 3D model such that the axis lies in a predefined orientation relative to and parallel with a plane of the means for display.

48. A computer program stored on computer-readable medium comprising code means that when executed on a computer carry out the steps of the means for processing of claim 47.

49. A computer program stored on computer-readable medium carrying code that when executed on a computer carry out the steps of the means for processing of claim 47.

* * * * *

UNITED STATES PATENT AND TRADEMARK OFFICE
CERTIFICATE OF CORRECTION

| | | |
|---|---|---|
| PATENT NO. | : 7,170,533 B2 | Page 1 of 1 |
| APPLICATION NO. | : 10/757859 | |
| DATED | : January 30, 2007 | |
| INVENTOR(S) | : Launay et al. | |

It is certified that error appears in the above-identified patent and that said Letters Patent is hereby corrected as shown below:

<u>Column 10</u>:
Line 2, after "as" delete "continued" and insert therefor -- confirmed --

Signed and Sealed this

Twenty-second Day of May, 2007

JON W. DUDAS
*Director of the United States Patent and Trademark Office*